(12) United States Patent
Fujita et al.

(10) Patent No.: US 9,333,705 B1
(45) Date of Patent: May 10, 2016

(54) ANVIL ROLLER AND ULTRASONIC WELDING DEVICE PROVIDED THEREWITH

(71) Applicant: ZUIKO CORPORATION, Settsu-shi, Osaka (JP)

(72) Inventors: Yukihiko Fujita, Osaka (JP); Hideyuki Nakamura, Osaka (JP)

(73) Assignee: ZUIKO CORPORATION, Settsu-shi, Osaka (JP)

( * ) Notice: Subject to any disclaimer, the term of this patent is extended or adjusted under 35 U.S.C. 154(b) by 0 days.

(21) Appl. No.: 14/893,596

(22) PCT Filed: Jun. 13, 2014

(86) PCT No.: PCT/JP2014/065807
§ 371 (c)(1),
(2) Date: Nov. 24, 2015

(87) PCT Pub. No.: WO2014/200103
PCT Pub. Date: Dec. 18, 2014

(30) Foreign Application Priority Data

Jun. 14, 2013 (JP) ................................. 2013-125942

(51) Int. Cl.
*B32B 37/00* (2006.01)
*B29C 65/08* (2006.01)
*B29C 65/00* (2006.01)
*B29C 65/78* (2006.01)

(52) U.S. Cl.
CPC ........... *B29C 65/086* (2013.01); *B29C 65/7885* (2013.01); *B29C 66/81431* (2013.01)

(58) Field of Classification Search
CPC .... B29C 65/08; B29C 65/083; B29C 65/086; B29C 65/087; B29C 65/088; B29C 65/7885; B29C 65/747; B29C 66/81431; B29C 66/0326; A61F 13/15585
USPC .................................. 156/73.1, 580.1, 580.2
See application file for complete search history.

(56) References Cited

U.S. PATENT DOCUMENTS

| 5,087,320 | A | 2/1992 | Neuwirth |
| 5,096,532 | A | 3/1992 | Neuwirth et al. |

(Continued)

FOREIGN PATENT DOCUMENTS

| JP | 5-131174 | 5/1993 |
| JP | 2001-236074 | 8/2001 |
| JP | 3988835 | 7/2007 |

OTHER PUBLICATIONS

International Search Report.

*Primary Examiner* — James Sells
(74) *Attorney, Agent, or Firm* — Gerald E. Hespos; Michael J. Porco; Matthew T. Hespos

(57) ABSTRACT

Provided is a lightweight anvil roller and an ultrasonic welding device provided therewith. The anvil roller has: a supported section that is rotatably supported by a holding mechanism via a rotary shaft in such a manner that the anvil roller can come into rolling contact with a sheet; an outer peripheral section having a welding surface over which the sheet is welded between the outer peripheral section and an ultrasonic horn during rolling contact with the sheet; a thin section that is formed between the supported section and the outer peripheral section in such a manner that the thickness of the thin section is smaller than the thickness of the outer peripheral section in the axial direction of the rotary shaft; and a vibration proof member provided on the thin section.

7 Claims, 6 Drawing Sheets

(56) References Cited

U.S. PATENT DOCUMENTS

| | | |
|---|---|---|
| 5,660,679 A | 8/1997 | Rajala et al. |
| 5,667,608 A | 9/1997 | Rajala et al. |
| 7,383,865 B2 * | 6/2008 | Umebayashi ..... A61F 13/15739 156/350 |
| 7,449,084 B2 * | 11/2008 | Nakakado ......... A61F 13/15739 156/580.1 |
| 7,658,053 B2 * | 2/2010 | Honegger ............... B29C 65/02 53/374.5 |
| 9,186,845 B2 * | 11/2015 | Shimada ........... A61F 13/15739 |

* cited by examiner

US 9,333,705 B1

ANVIL ROLLER AND ULTRASONIC WELDING DEVICE PROVIDED THEREWITH

TECHNICAL FIELD

The present invention relates to an anvil roller that is used for ultrasonically welding an object to be welded, and to an ultrasonic welding device that is provided with the anvil roller.

BACKGROUND ART

Conventional ultrasonic welding devices include ultrasonic welding devices each provided with an anvil and an ultrasonic horn, wherein an object to be welded is sandwiched between the anvil and the ultrasonic horn, and in that state, ultrasonic vibration is applied to the ultrasonic horn, to weld as a result the object to be welded.

Known ultrasonic welding devices of that type include ultrasonic welding devices each provided with a holding member that holds an object to be welded, and an anvil roller that can move with respect to a holding member, between a welding position at which the object to be welded, held on the holding member, is welded between the ultrasonic horn and the anvil roller, and a separation position that is spaced apart from the object to be welded (for instance, Japanese Patent No 3988835).

The anvil roller disclosed in Japanese Patent No 3988835 is rotatably supported about a predetermined rotation axis so that the anvil roller can come into rolling contact with the object to be welded, during the movement of the anvil roller.

A demand exists for a lighter anvil roller, in order to reduce the load and power that is imparted to a support mechanism, in a case where the anvil roller is supported movably with respect to the object to be welded, as in the ultrasonic welding device disclosed in Japanese Patent No 3988835.

SUMMARY OF INVENTION

It is an object of the present invention to provide a lightweight anvil roller, and an ultrasonic welding device that is provided therewith.

The present invention provides an anvil roller, used in an ultrasonic welding device that includes: a holding member that holds an object to be welded; an ultrasonic horn that applies ultrasonic vibration to the object to be welded held by the holding member; an anvil roller for welding the object to be welded, between the ultrasonic horn and the anvil roller; and a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member, the anvil roller including: a supported section that is rotatably supported by the holding mechanism via the rotary shaft; an outer peripheral section having a welding surface over which the object to be welded can be welded between the ultrasonic horn and the outer peripheral section during rolling contact with the object to be welded; a thin section that is formed between the supported section and the outer peripheral section in such a manner that the thickness of the thin section is smaller than the thickness of the outer peripheral section in an axial direction of the rotary shaft; and a vibrationproof member provided on the thin section.

The present invention further provides an ultrasonic welding device that is provided with: a holding member that holds an object to be welded; an ultrasonic horn that applies ultrasonic vibration to the object to be welded held by the holding member; the anvil roller for welding the object to be welded, between the ultrasonic horn and the anvil roller; and a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member.

The present invention allows reducing the weight of an anvil roller.

DESCRIPTION OF EMBODIMENTS

The embodiments of the present invention are described hereinbelow by referring to the attached figures. The following embodiments are examples substantiating the present invention and do not limit the technical scope of the present invention.

Figure 1:
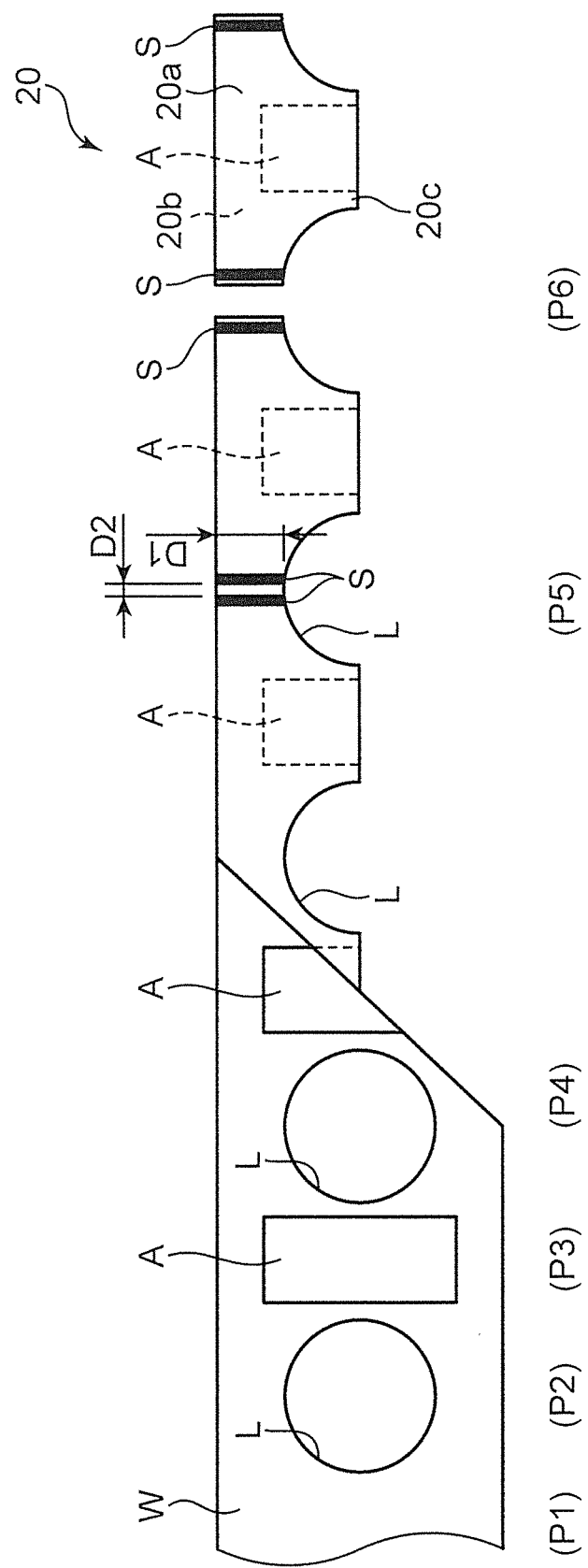
FIG. 1 is a process diagram for explaining a method of producing a disposable diaper using an ultrasonic welding device according to the present invention.

With reference to FIG. 1, a disposable diaper 20 includes, when worn, a front abdominal section 20a disposed on the abdomen of the wearer, a rear dorsal section 20b disposed on the buttocks of the wearer, and a crotch section 20c that extends from the front abdominal section 20a, passing between the legs of the wearer, up to the rear dorsal section 20b.

Both side edge portions of the front abdominal section 20a and both side edge portions of the rear dorsal section 20b are welded to each other by two weld sections S, in such a manner that the front abdominal section 20a and the rear dorsal section 20b are connected in the form of a ring.

A method of producing the disposable diaper 20 will be explained next.

<Transport Step P1>

In the transport step P1, a sheet W that extends in a specific direction is transported along the length direction of the sheet W. In the explanation hereafter, the flow direction of the sheet W will be referred to as transversal direction, and the direction perpendicular to the transversal direction in FIG. 1 will be referred to as longitudinal direction.

The sheet W has an inner sheet that faces the body surface of the wearer when the wearer wears the diaper, an outer sheet that faces away from the wearer when the wearer wears the diaper, and an elastic member that is sandwiched between the inner sheet and the outer sheet.

The inner sheet is constituted by a nonwoven fabric sheet and/or a mesh sheet having liquid permeability. The outer sheet is constituted by a material, identical to that of the inner sheet, a polyethylene film, a polypropylene film, or a nonwoven fabric having water repellency and breathability.

The elastic member is constituted by a sheet or thread made of polyurethane, natural rubber, or a thermoplastic resin.

<Leg Hole Forming Step P2>

In the leg hole forming step P2, leg holes L are formed at a central position of the sheet W in the longitudinal direction.

Each region between the two leg holes L in the sheet W is a portion corresponding to the crotch section 20c. The positions on both sides of each portion in the sheet W corresponding to the crotch section 20c, in the longitudinal direction, correspond herein to the front abdominal section 20a and the rear dorsal section 20b, respectively.

<Absorbent Body Bonding Step P3>

In the absorbent body bonding step P3, an absorbent body A is bonded at a position in the sheet W between the two leg holes L.

The absorbent body A includes a permeable sheet having liquid permeability, a water-repellent sheet having water-repellency and breathability, and an absorbent core sandwiched between the permeable sheet and the water-repellent sheet.

The permeable sheet is constituted by a nonwoven fabric sheet and/or a mesh sheet having liquid permeability. The water-repellent sheet is constituted by a polyethylene film, a polypropylene film, or a nonwoven fabric having water-repellency and breathability.

The absorbent core is molded through layering of crushed pulp or crushed pulp mixed with a high water-absorbing polymer.

A method is explained herein where the absorbent body A is bonded to the sheet W, but the absorbent core may be bonded in a state where the absorbent core is sandwiched between the inner sheet and the outer sheet of the sheet W. In this case, the inner sheet is constituted by a nonwoven fabric sheet and/or a mesh sheet having liquid permeability. The outer sheet is constituted by a polyethylene film, a polypropylene film, or a nonwoven fabric having water-repellency and breathability.

<Fold-in-half Step P4>

In the fold-in-half step P4, the sheet W (continuous body) having the absorbent body A placed thereon is folded in half in the longitudinal direction. As a result, the portion of the sheet W corresponding to the front abdominal section 20a and the portion corresponding to the rear dorsal section 20b are overlapped on each other.

<Welding Step P5>

In the welding step P5, a portion of the folded sheet W corresponding to a side edge portion of the front abdominal section 20a and the portion corresponding to a side edge portion of the rear dorsal section 20b are ultrasonically welded.

In the welding step P5, specifically, two sites of the sheet W are ultrasonically welded simultaneously, with a spacing D2 including a predetermined cutting range as a range of cutting in the cutting step P6 described below.

The two weld sections S are respectively formed over a welding range D1 in the longitudinal direction of a portion corresponding to a side edge portion of the front abdominal section 20a, and a portion corresponding to a side edge portion of the rear dorsal section 20b.

<Cutting Step P6>

In the cutting step P6, the sheet W is cut along a respective cutting line that extends, in the longitudinal direction, between two weld sections S formed in the welding step P5. The sheet W (continuous body) is cut as a result into each disposable diaper 20.

Figure 2:
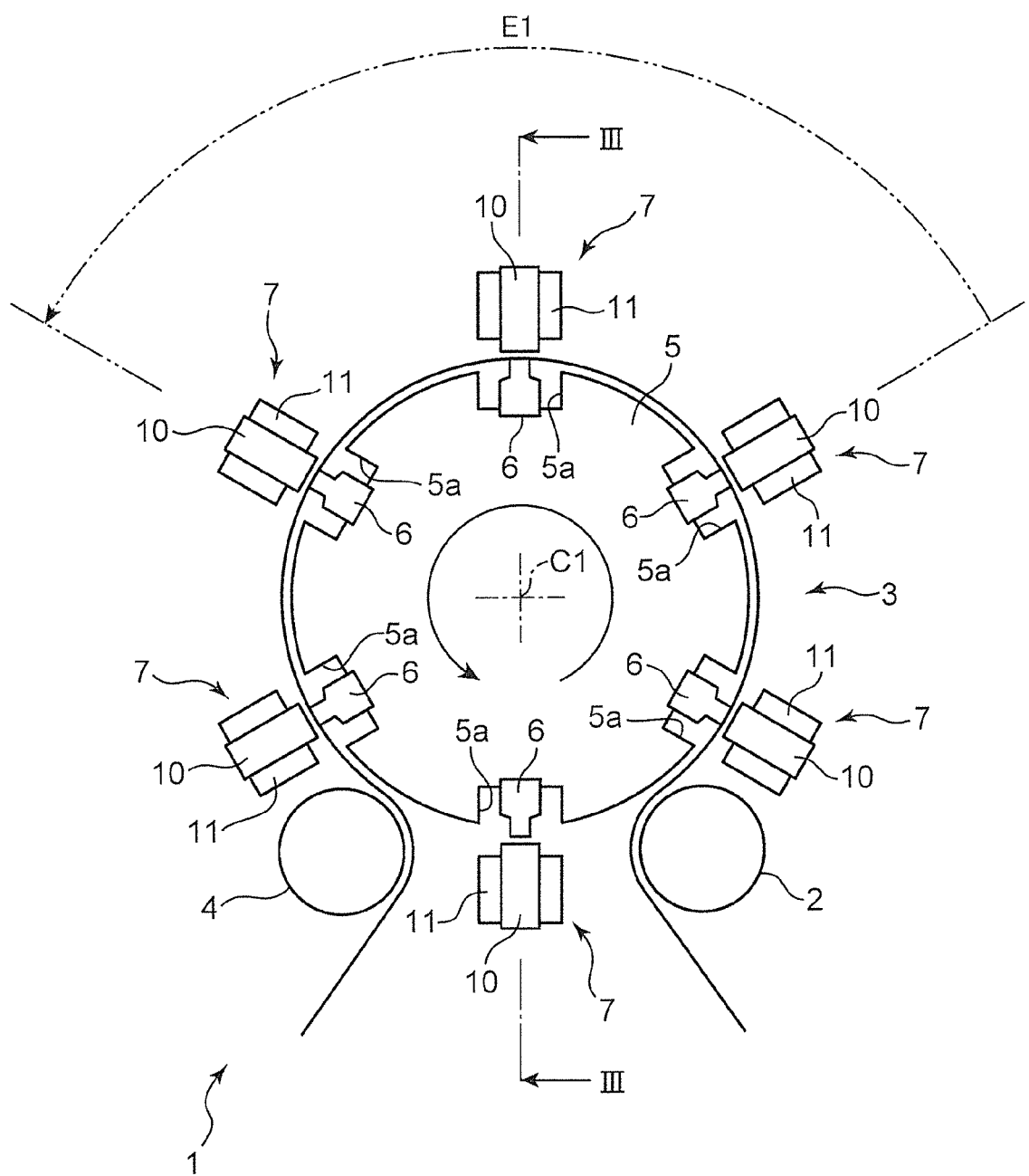
FIG. 2 is a front-view diagram illustrating the schematic configuration of an ultrasonic welding device according to a first embodiment of the present invention, for carrying out the welding step illustrated in FIG. 1.

An explanation follows next, with reference to FIG. 2, on an ultrasonic welding device 1, according to the first embodiment, that carries out the welding step P5.

The ultrasonic welding device 1 is provided with an introduction roller 2 that introduces the folded sheet W undergone the fold-in-half step P4; a welding drum 3 that welds the sheet W that is introduced by the introduction roller 2; and a lead-out roller 4 that leads out the sheet W welded by the welding drum 3.

The welding drum 3 is provided with: a sheet holding drum (holding member) 5 that holds the sheet (object to be welded) W that is introduced by the introduction roller 2; six ultrasonic horns 6 that are provided on the sheet holding drum 5; six anvil units 7 for ultrasonically welding the sheet W between the ultrasonic horns 6 and respective anvil units 7; a cylindrical anvil holding drum 8 (see FIG. 3) that holds the anvil units 7; and a cam drum 9 (see FIG. 3) provided inside the anvil holding drum 8.

Figure 3:
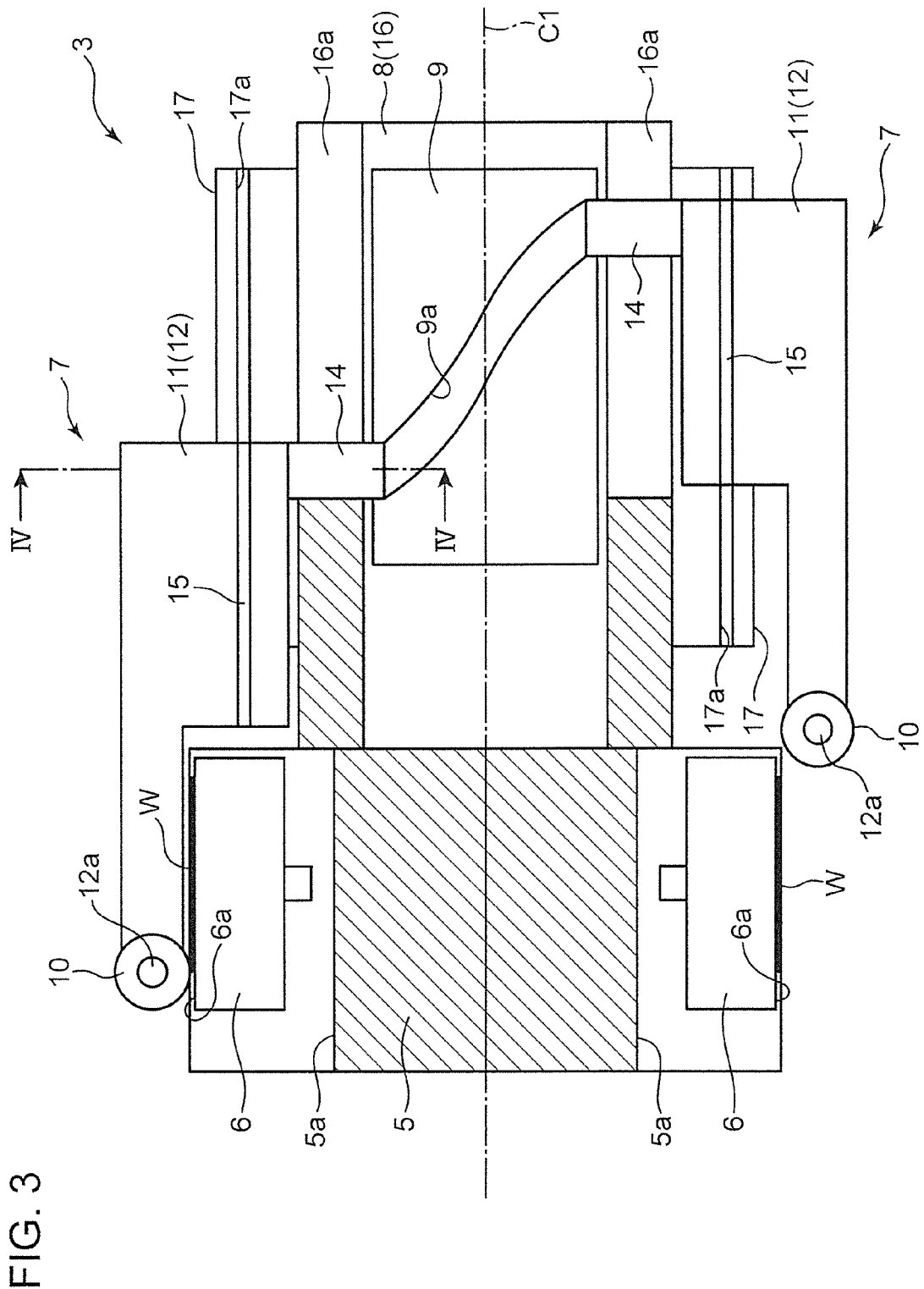
FIG. 3 is a cross-sectional diagram of FIG. 2 along line III-III.

With reference to FIG. 2 and FIG. 3, the sheet holding drum 5 can rotate about a rotation center C1 in a state where the sheet W is held on the outer peripheral surface of the sheet holding drum 5. Six recessed grooves 5a are formed equidistantly, about the rotation center C1, on the sheet holding drum 5. The recessed grooves 5a open outward from the sheet holding drum 5 and extend along the rotation center C1.

The ultrasonic horns 6 impart ultrasonic vibration to the sheet W that is held on the sheet holding drum 5. Specifically, the ultrasonic horns 6 are provided in respective recessed grooves 5a, in such a manner that welding surfaces 6a of the ultrasonic horns 6 come in contact, from inside, with the sheet W that is held on the sheet holding drum 5.

Each of the anvil units 7 is provided at position identical to each of the ultrasonic horns 6, about the rotation center C1. The anvil units 7 have all the same configuration; hence, the configuration of just one of anvil unit 7 will be explained, and a explanation of the other anvil units 7 will be omitted.

Anvil unit 7 is provided with an anvil roller 10 for welding the sheet W between the ultrasonic horn 6 and the anvil roller 10, and a holding mechanism 11 that holds rotatably the anvil roller 10, via a rotary shaft 12a, in such a manner that the anvil roller 10 can be in rolling contact with the sheet W, in response to the displacement of the anvil roller 10 with respect to the sheet holding drum 5.

Figure 4:
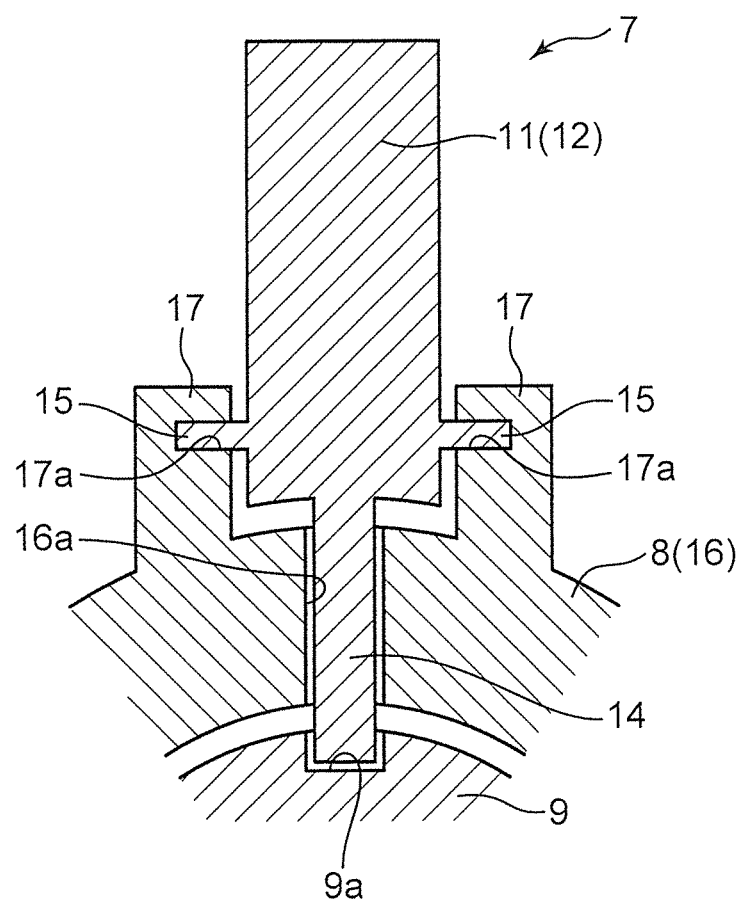
FIG. 4 is a cross-sectional diagram of FIG. 3 along line IV-IV.

As illustrated in FIG. 3 and FIG. 4, holding mechanism 11 is provided with: a body section 12 that holds the anvil roller 10; a cam protrusion 14 that extends from the body section 12 toward the rotation center C1; and a pair of engaging protrusions 15 that protrude from the body section 12, in opposite orientations in a direction (left-right direction in FIG. 4) perpendicular to the cam protrusion 14 and the rotation center C1, and that extend along the rotation center C1.

The body section 12 is provided between a pair of rails 17 that are standed on the outer peripheral surface of the anvil holding drum 8. In the rails 17, engaging grooves which open toward counterpart rails 17 and which extend along the rotation center C1 are formed. The engaging protrusions 15 of the body section 12 engage with respective engaging grooves 17a in such a manner that the engaging protrusions 15 can move along the rotation center C1, with respect to anvil holding drum 8.

The cylindrical anvil holding drum 8 is provided with slits 16a that penetrate through the peripheral wall of the cylindrical anvil holding drum 8 and that extend along the rotation center C1. The cam protrusions 14 of the body sections 12 are inserted into the anvil holding drum 8 via respective slits 16a.

The cam drum 9 is provided inside the anvil holding drum 8, and a cam groove 9a is formed on the outer peripheral surface of the cam drum 9. The leading end sections of the cam protrusions 14 are inserted into the cam groove 9a. The cam groove 9a guides the cam protrusions 14 in such a manner that the anvil units 7 move along the rotation center C1, in response to the rotation of the anvil holding drum 8 with respect to the cam drum 9.

The sheet holding drum 5 and the anvil holding drum 8 are fixed to each other and rotate integrally about the rotation center C1. By contrast, the rotational position of the cam drum 9 is fixed, regardless of the rotation of the sheet holding drum 5 and the anvil holding drum 8. Therefore, the body section 12 moves along the rotation center C1 in response to rotation of the sheet holding drum 5 and the anvil holding drum 8 about the rotation center C1.

That is, the holding mechanism 11 and the anvil holding drum 8 correspond to a support mechanism that supports rotatably each anvil roller 10, via the rotary shaft 12a, in such a manner that the anvil roller 10 can move along the rotation center C1 with respect to the sheet holding drum 5, and the anvil roller 10 can be in rolling contact with the sheet W in response to the movement of the anvil roller 10 with respect to the sheet holding drum 5.

Specifically, in the anvil unit 7 positioned lowermost in FIG. 2 and FIG. 3, the anvil roller 10 is disposed at a separation position that is spaced apart from the sheet W held by the sheet holding drum 5. In this state, the anvil unit 7 moves in a direction of coming close to the sheet W along the rotation center C1, in response to the counter-clockwise rotation, in FIG. 2, of the sheet holding drum 5.

The anvil roller 10 crosses over the sheet W when the anvil unit 7 is displaced up to the topmost position in FIG. 2 and the FIG. 3. When the sheet holding drum 5 further rotates counter-clockwise from this state, the anvil unit 7 starts moving toward the separation position.

In the ultrasonic welding device 1, thus, each anvil roller 10 reciprocates over the sheet W, in the welding range D1 of FIG. 1, within the range E1 of FIG. 2. The sheet W is welded during this reciprocating movement. The position of each anvil roller 10 with respect to the sheet holding drum 5 in the range E1 corresponds to a welding position.

Figure 5:
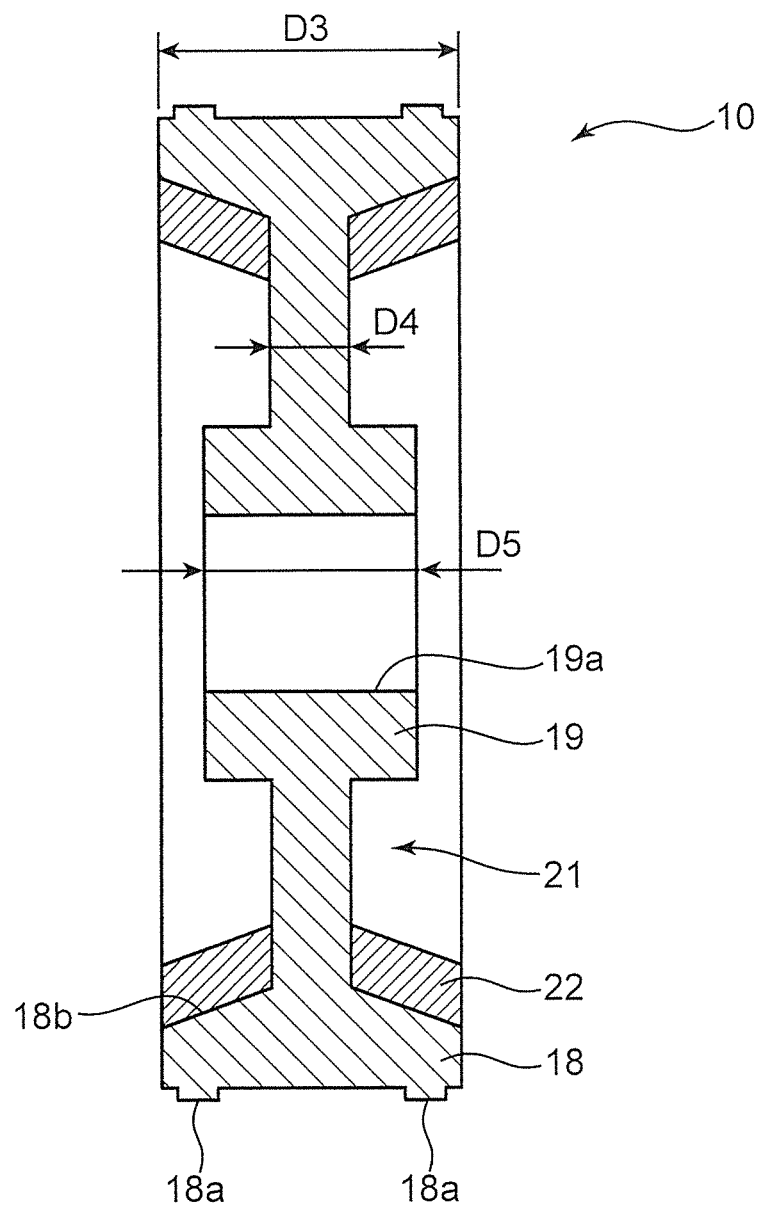
FIG. 5 is a front-view cross-sectional diagram of an anvil roller illustrated in FIG. 4.

The anvil rollers 10 will be explained next with respect to FIG. 3 and FIG. 5.

The anvil rollers 10 are rollers made of metal (for instance, high-chromium steel, or high-carbon steel).

Each anvil roller 10 is provided with a supported section 19 that is rotatably supported by the holding mechanism 11, via the rotary shaft 12a; an outer peripheral section 18 over which the sheet W can be welded between the ultrasonic horn 6 and the outer peripheral section 18 during rolling contact with the sheet W; a thin section 21 that is provided between the supported section 19 and the outer peripheral section 18; and two vibrationproof members 22 that are provided on the thin section 21.

The supported section 19 is a boss portion that is rotatably supported, via the rotary shaft 12a, by the holding mechanism 11, in order to allow rolling contact of the anvil roller 10 with the sheet W in response to the movement of the anvil roller 10 between the welding position and the separation position. A through-hole 19a for insertion of the rotary shaft 12a is formed in the supported section 19.

The outer peripheral section 18 has a welding surface over which the sheet W can be welded between the ultrasonic horn 6 and the outer peripheral section 18 during rolling contact with the sheet W. Specifically, the outer peripheral section 18 has a pair of welding sections 18a that protrude outward, in the diameter direction of the outer peripheral section 18, and that extend over the entire circumference about the rotary shaft 12a. The spacing between the welding sections 18a corresponds to the spacing D2 of the weld section S in FIG. 1. That is, the outer peripheral surface of the welding sections 18a corresponds to the welding surface over which the sheet W is welded between the welding sections 18a and the ultrasonic horn 6.

The thin section 21 is a portion that is formed through recessing of the anvil roller 10 from both sides in the axial direction of the rotary shaft 12a.

A thickness dimension D4 of the thin section 21, in the axial direction of the rotary shaft 12a, is smaller than a thickness dimension D5 of the supported section 19 and a thickness dimension D3 of the outer peripheral section 18. The thickness dimension D5 of the supported section 19 is smaller than the thickness dimension D3 of the outer peripheral section 18.

As a result, the weight of the anvil roller 10 can be reduced as compared with a cylindrical anvil roller having just the through-hole 19a alone formed therein.

The thin section 21 is provided over the entire circumference about the rotary shaft 12a.

The vibrationproof members 22 are formed of a material that can deform elastically (for instance, a rubber material such as silicon rubber or synthetic rubber, or a synthetic resin material). By deforming elastically, the vibrationproof members 22 reduce the vibration of the anvil roller 10.

The two vibrationproof members 22 are bonded to two respective reverse faces 18b, with respect to the welding surface of the outer peripheral section 18, as defined by the thin section 21. The reverse faces 18b are tilted by an angle of 20° with respect to the axis of the rotary shaft 12a, and the vibrationproof members 22 are provided over the entire circumference of the reverse faces 18b about the rotary shaft 12a.

The vibrationproof members 22 are provided only over part of the thin section 21. That is, the vibrationproof members 22 are formed over a given thickness in the entire circumference about the rotary shaft 12a. A clearance is thus formed between the vibrationproof members 22 and the supported section 19.

As explained above, vibration in the anvil roller 10 can be suppressed by the vibrationproof members 22 that are provided on the thin section 21. Accordingly, it becomes possible to reduce the weight of the anvil roller 10, through formation of the thin section 21, and, at the same time, to prevent the occurrence of noise that accompanies this reduction in weight.

The following effects can be obtained according to the above embodiment.

According to the above embodiments, the vibrationproof members 22 are provided on the reverse faces 18b with respect to the welding surface (outer peripheral surface of the welding sections 18a) that receives ultrasonic vibration from the ultrasonic horn 6. As a result, vibration of the anvil roller 10 can be suppressed efficiently at a position in the immediate vicinity of a vibration source.

According to the above embodiment, the thin section 21 is provided over the entire circumference about the rotary shaft 12a; as a result, the weight of the anvil roller 10 about the rotary shaft 12a is equalized, and the rotational stability of the anvil roller 10 can be increased thereby.

Therefore, the above embodiment allows reducing, more reliably, generation of noise due to vibration of the anvil roller 10, thanks to of the noise reduction effect derived from the rotational stability of the anvil roller 10, and the noise reduction effect derived from the vibrationproof members 22 that are provided over the entire circumference about the rotary shaft 12a.

According to the above embodiment, the vibrationproof members 22 are provided only over part of the thin section 21; accordingly, this allows suppressing an increase in the weight of the anvil roller 10 caused by an excessively large vibrationproof member.

According to the above embodiment, the thickness dimension D5 of the supported section 19 is greater than the thickness dimension D4 of the thin section 21. Accordingly, the strength of the supported section 19 that is supported by the rotary shaft 12a can be secured, while reducing the weight of the anvil roller 10 thanks to the thin section 21.

By setting the thickness dimension D5 of the supported section 19 to be smaller than the thickness dimension D3 of the outer peripheral section 18, it becomes possible to reduce the weight of the anvil roller 10 while securing the necessary strength in the supported section 19.

Figure 6:
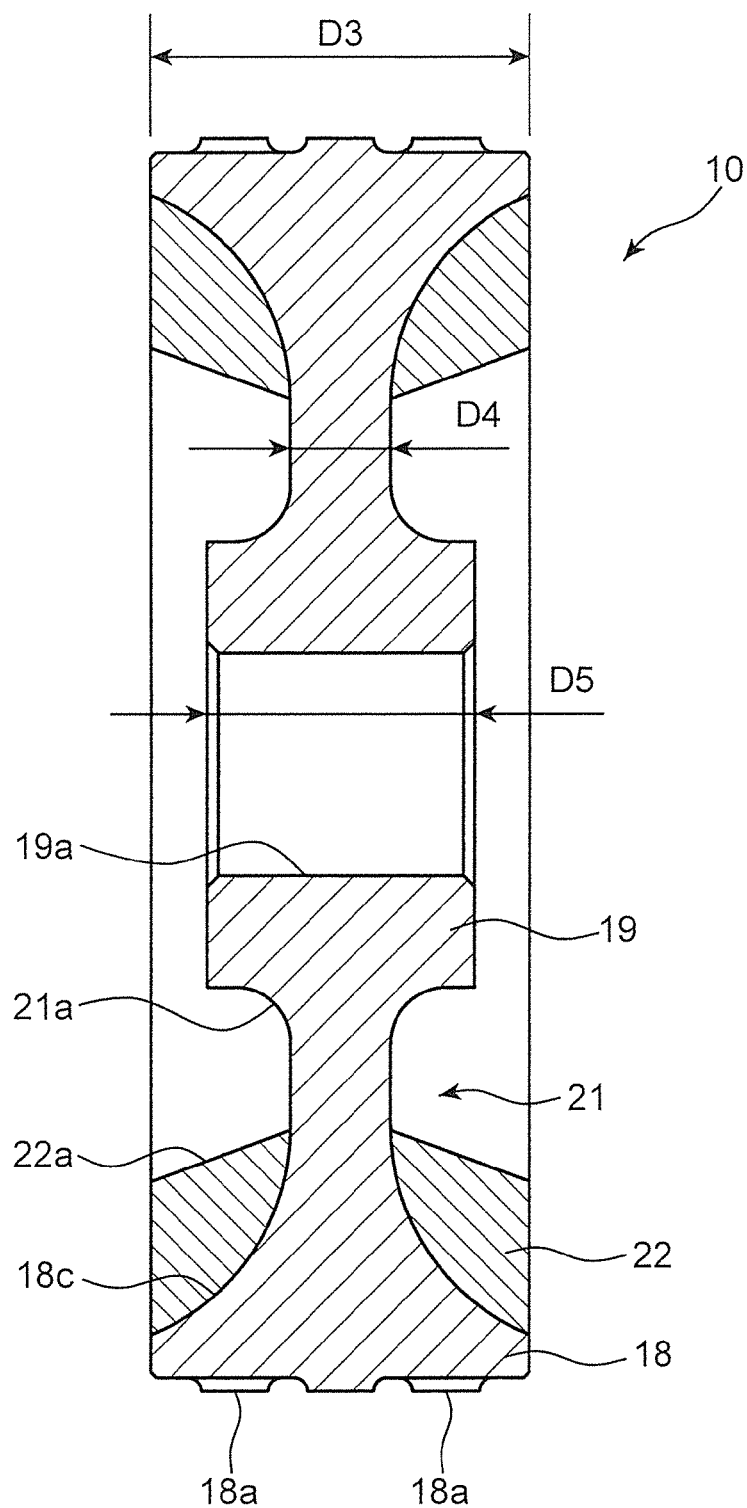
FIG. 6 is a diagram, corresponding to FIG. 5, illustrating an anvil roller of an ultrasonic welding device according to a second embodiment of the present invention.

The anvil roller 10 of an ultrasonic welding device according to a second embodiment of the present invention will be explained next with reference to FIG. 6. Portions identical to those in the first embodiment will be denoted by the same reference symbols, and an explanation thereof will be omitted.

The anvil roller 10 according to the second embodiment is provided with a rounded section 18c that is formed between the outer peripheral section 18 and the thin section 21, and a rounded section 21a that is formed between the thin section 21 and the supported section 19.

The rounded sections 18c, 21a are provided over the entire circumference about the rotary shaft 12a (see FIG. 3).

The outer peripheral section 18 and the supported section 19 are connected to the thin section 21 via the rounded sections 18c, 21a. Abrupt changes in the cross-sectional area of the anvil roller 10 between the thin section 21 and the outer peripheral section 18, and between the thin section 21 and the supported section 19, can be suppressed as a result.

Therefore, it becomes possible to suppress concentration of stress at the boundary portions between the thin section 21 and the outer peripheral section 18, and between the thin section 21 and the supported section 19, upon application of ultrasonic vibration from the ultrasonic horn 6 to the anvil roller 10. The fatigue strength of the anvil roller 10 can be enhanced as a result.

Herein there may be provided just one from among the rounded sections 18c, 21a, in which case a fatigue strength enhancing effect can be elicited by the one of the rounded sections.

In the anvil roller 10 according to the second embodiment, the vibrationproof members 22 are provided so as to be in close contact with the entire surface of the rounded section 18c. In the vibrationproof members 22, inner surfaces 22a that face toward the supported section 19 are tilted by an angle of 20° with respect to the axis of the rotary shaft 12a, as in the first embodiment.

In the above embodiments, the vibrationproof members 22 are provided only over part of the thin section 21, but the vibrationproof members 22 may be provided over the entire range of the thin section 21. For instance, the vibrationproof members 22 can be filled up into the thin section 21.

In the above embodiments, anvil rollers 10 have been explained that have the welding surface (welding sections 18a) provided over a 360° area about the rotary shaft 12a, but the formation area of the welding surface can be set to less than 360° about the rotary shaft 12a.

Specifically, the formation area (angle) of the welding surface can be set to have a circumferential length that exceeds the welding range D1 (FIG. 1) of the sheet W. For instance, a semi-circular anvil roller can be used herein.

Using circular anvil rollers 10 having a circumferential length that exceeds the welding range D1 of the sheet W, as in the above embodiments, has the following advantage. The frequency of replacement of the anvil roller 10, in a case where, for instance, part of the welding surface of the anvil roller 10 is damaged, can be reduced through adjustment of the mounting position of the anvil roller 10 in such a manner that welding can be carried out using a portion other than the damaged portion.

The specific embodiments described above include an invention having the following features.

In order to solve the above problems, the inventors of the present application conceived of an invention pertaining to an anvil roller in which a thin section is formed between an outer peripheral section having a welding surface and a supported section that is supported by a rotary shaft, the thickness of the thin section being smaller than the thickness of the outer peripheral section.

When the weight of the anvil roller is thus reduced through formation of the thin section, however, the natural frequency of the anvil roller increases, and a new problem arises thereupon, namely the occurrence of noise derived from resonance of the anvil roller when the anvil roller receives ultrasonic vibration from the ultrasonic horn.

In order to solve this new problem, therefore, the present invention provides an anvil roller, used in an ultrasonic welding device that includes: a holding member that holds an object to be welded; an ultrasonic horn that applies ultrasonic vibration to the object to be welded held by the holding member; an anvil roller for welding the object to be welded, between the ultrasonic horn and the anvil roller; and a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member, the anvil roller including: a supported section that is rotatably supported by the holding mechanism via the rotary shaft; an outer peripheral section having a welding surface over which the object to be welded can be welded between the ultrasonic horn and the outer peripheral section during rolling contact with the object to be welded; a thin section that is formed between the supported section and the outer peripheral section in such a manner that the thickness of the thin section is smaller than the thickness of the outer peripheral section in an axial direction of the rotary shaft; and a vibrationproof member provided on the thin section.

According to the present invention, vibration occurring in the anvil roller can be suppressed by the vibrationproof member that is provided on the thin section. Accordingly, it becomes possible to reduce the weight of the anvil roller, through formation of the thin section, and, at the same time, to prevent the occurrence of noise that accompanies this reduction in weight.

In the anvil roller, preferably, the vibrationproof member is provided on a reverse face, with respect to the welding surface, of the outer peripheral section, as defined by the thin section.

In this aspect, the vibrationproof member is provided on the reverse face with respect to the welding surface that receives the ultrasonic vibration from the ultrasonic horn.

Accordingly, vibration of the anvil roller can be suppressed efficiently at a position in the immediate vicinity of a vibration source.

In the anvil roller, preferably, the thin section is provided over the entire circumference about the rotary shaft, and the vibrationproof member is provided over the entire circumference of the reverse face about the rotary shaft.

In this aspect, the thin section is provided over the entire circumference about the rotary shaft; as a result, the weight of the anvil roller about the rotary shaft is equalized, and the rotational stability of the anvil roller can be increased thereby.

Therefore, the above aspect allows reducing generation of noise due to vibration of the anvil roller more reliably, by virtue of the noise reduction effect derived from the rotational stability of the anvil roller, and the noise reduction effect derived from the vibrationproof member that is provided over the entire circumference about the rotary shaft.

The vibrationproof member can be filled up into the entirety of a groove of the anvil roller that is defined by the thin section, but, preferably, the vibrationproof member is provided only over part of the thin section.

This aspect allows suppressing an increase in the weight of the anvil roller caused by an excessively large vibrationproof member.

In the anvil roller, preferably, the thickness of the supported section is greater than the thickness of the thin section in the axial direction of the rotary shaft.

In this aspect, the strength of the supported section that is supported by the rotary shaft can be secured, while reducing the weight of the anvil roller by virtue of the thin section.

By setting the thickness of the supported section to be smaller than the thickness of the outer peripheral section, it becomes possible to reduce the weight of the anvil roller while securing the necessary strength in the supported section.

The present invention further provides an ultrasonic welding device that is provided with: a holding member that holds an object to be welded; an ultrasonic horn that applies ultrasonic vibration to the object to be welded held by the holding member; the anvil roller for welding the object to be welded, between the ultrasonic horn and the anvil roller; and a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member.

The invention claimed is:

1. An anvil roller, used in an ultrasonic welding device that includes: a holding member that holds an object to be welded; an ultrasonic horn that applies ultrasonic vibration to the object to be welded held by the holding member; an anvil roller for welding the object to be welded between the ultrasonic horn and the anvil roller; and a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member, the anvil roller comprising:
   a supported section that is rotatably supported by the holding mechanism via the rotary shaft;
   an outer peripheral section having a welding surface over which the object to be welded can be welded between the ultrasonic horn and the outer peripheral section during rolling contact with the object to be welded;
   a thin section that is formed between the supported section and the outer peripheral section in such a manner that the thickness of the thin section is smaller than the thickness of the outer peripheral section in an axial direction of the rotary shaft; and
   a vibrationproof member provided on the thin section.

2. The anvil roller according to claim 1, wherein the vibrationproof member is provided on a reverse face, with respect to the welding surface, of the outer peripheral section, as defined by the thin section.

3. The anvil roller according to claim 2,
   wherein the thin section is provided over the entire circumference about the rotary shaft, and
   the vibrationproof member is provided over the entire circumference of the reverse face about the rotary shaft.

4. The anvil roller according to claim 2, wherein the vibrationproof member is provided only over part of the thin section.

5. The anvil roller according to claim 1, wherein the thickness of the supported section is greater than the thickness of the thin section in the axial direction of the rotary shaft.

6. The anvil roller according to claim 5, wherein the thickness of the supported section is smaller than the thickness of the outer peripheral section.

7. An ultrasonic welding device, comprising:
   a holding member that holds an object to be welded;
   an ultrasonic horn that applies ultrasonic vibration to the object to be welded held by the holding member;
   the anvil roller according to claim 1, for welding the object to be welded, between the ultrasonic horn and the anvil roller; and
   a support mechanism that supports the anvil roller via a rotary shaft in such a manner that the anvil roller can move with respect to the holding member, and that the anvil roller can come into rolling contact with the object to be welded in response to the movement of the anvil roller with respect to the holding member.

* * * * *